United States Patent
Auer et al.

(10) Patent No.: US 7,399,583 B2
(45) Date of Patent: Jul. 15, 2008

(54) METHOD FOR THE IDENTIFICATION OF INHIBITORS OF THE BINDING OF ARE-CONTAINING MRNA AND A HUR PROTEIN

(75) Inventors: Manfred Auer, Moedling (AT); Nicole-Claudia Meisner, Vienna (AT); Volker Uhl, Maria Enzersdorf (AT)

(73) Assignee: Novartis AG, Basel (CH)

( * ) Notice: Subject to any disclaimer, the term of this patent is extended or adjusted under 35 U.S.C. 154(b) by 337 days.

(21) Appl. No.: 10/510,413

(22) PCT Filed: Apr. 16, 2003

(86) PCT No.: PCT/EP03/04008

§ 371 (c)(1), (2), (4) Date: May 27, 2005

(87) PCT Pub. No.: WO03/087815

PCT Pub. Date: Oct. 23, 2003

(65) Prior Publication Data

US 2006/0008802 A1 Jan. 12, 2006

Related U.S. Application Data

(60) Provisional application No. 60/373,207, filed on Apr. 17, 2002.

(51) Int. Cl.
*G01N 33/53* (2006.01)
(52) U.S. Cl. .............................. 435/4; 435/6
(58) Field of Classification Search ................ None
See application file for complete search history.

(56) References Cited

U.S. PATENT DOCUMENTS

| 6,180,604 B1 | 1/2001 | Fraser et al. .................. 514/12 |
| 6,436,636 B1 | 8/2002 | Port et al. ...................... 435/6 |
| 2002/0165186 A1 | 11/2002 | Hauber et al. ................. 514/44 |

FOREIGN PATENT DOCUMENTS

| EP | 0 873 998 | 10/1998 |
| WO | 93/23531 | 11/1993 |
| WO | 98/04923 | 2/1998 |
| WO | 98/39484 | 9/1998 |
| WO | 99/61605 | 12/1999 |
| WO | 00/39314 | 7/2000 |
| WO | 00/67023 | 11/2000 |
| WO | 01/12213 | 2/2001 |
| WO | 01/34624 | 5/2001 |
| WO | 01/48193 | 7/2001 |
| WO | 01/83691 | 11/2001 |

OTHER PUBLICATIONS

Myer, et al. Identification of HuR as a protein implicated in AUUUA-mediated mRNA decay. EMBO J. Apr. 15, 1997;16(8):2130-9.*
Ausserlechner et al., "Chemiluminescence-Based RNase Protection Assays for Simulaneous Quantification of Procollagen mRNAs Containing AU-Rich Regions", BioTechniques, vol. 24, pp. 366-370 (1998).
Chrzanowska-Lightowlers et al., "Fending off Decay: A Combinatorial Approach in Intact Cells for Identifyign mRNA Stability Elements", RNA, vol. 7, pp. 435-444 (2001).
Fritz et al., "An in Vitro Assay to Study Regulated mRNA Stability", Science's Stke, vol. 61, PL1, pp. 1-13 (2000).
Brennan et al., "Protein Ligands to HuR Modulate its Interaction with Target mRNAs In Vivo", J. Cell Biol., vol. 151, No. 1, pp. 1-13 (2000).
Guhaniyogi et al., "Regulation of mRNA Stability in Mammalian Cells", Gene, vol. 265, No. 1-2, pp. 11-23 (2001).
Ma et al., "Cloning and Characterization of Hur, a Ubiquitously Expressed Elav-like Protein", J. Biol. Chem., vol. 271, No. 14, pp. 8144-8151 (1996).
Peng et al., "RNA Stabilization by the Au-rich Element Binding Protein, HuR, an ELAV Protein", EMBO (Eur. Mol. Biol. Organ.) J., vol. 17, No. 12, pp. 3461-3470 (1998).

* cited by examiner

*Primary Examiner*—Prema M Mertz
(74) *Attorney, Agent, or Firm*—John Prince

(57) ABSTRACT

The present invention provides for a method for identifying an agent that has an inhibitory effect on the complex-formation of an ARE-containing mRNA and an HuR protein.

5 Claims, 1 Drawing Sheet

Figure 1:
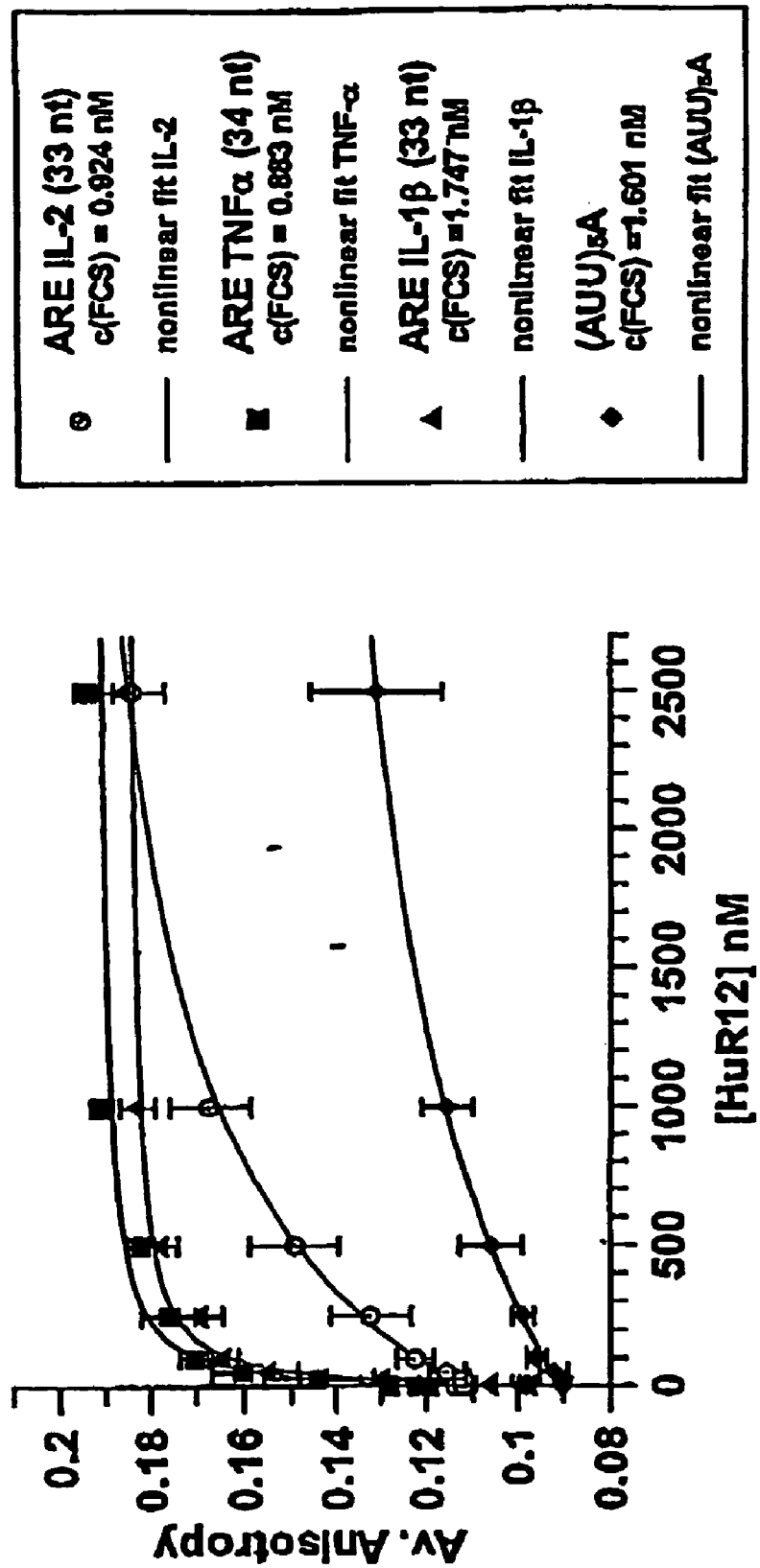

METHOD FOR THE IDENTIFICATION OF INHIBITORS OF THE BINDING OF ARE-CONTAINING MRNA AND A HUR PROTEIN

This application claims benefit of U.S. Provisional Application No. 60/373,207, filed Apr. 17, 2002, which in its entirety is herein incorporated by reference.

The present invention relates to compound screening, e.g. to assays and methods for identifying candidate compounds that have an inhibitory effect on the complex-formation of an AU-rich elements (AREs)-containing mRNA and an HuR protein.

Regulation of mRNA stability is recognized as a crucial mechanism for controlling eukaryotic gene expression at a posttranscriptional level. While long-lived mRNAs are buffered against rapid changes with respect to the production of a specific gene product, a short mRNA half-life is essential to permit timely adjustments to changing physiological conditions and to cellular, often receptor-mediated, signals. It has been found that half-lives of messages from inflammatory cytokines, growth factors and several proto-oncogenes are subjected to tight control mechanisms often mediated by AREs.

mRNAs from many disease-relevant early-response genes (ERGS) are targeted for specific degradation by the presence of AREs in the 3'-untranslated region (UTR). Because of the relevance of proteins encoded by ARE-containing mRNAs, this element must be considered a pivotal target for anti-inflammatory therapies but also for targets of essentially different relevance like proto-oncogenes such as e.g. c-fos, c-myc as well as bcl-2. Particularly the mRNAs of cytokines and proto-oncogenes are targeted in cis for degradation by AREs in their 3'-UTR, mediated by trans-acting factors or proteins binding to them.

AREs are basically characterized by the presence of the pentameric consensus motif AUUUA. However, the ARE-sequences differ from each other by the arrangement and number of these pentanucleotides. Moreover, the number, length and position of the ARE within the 3'-UTR is highly variable. Whereas multiple AUUUA sequences in close proximity or AU-rich regions have been implicated in mRNA instability, isolated AUUUA sequences may in contrast have other regulatory functions, for example in translation and mRNA localization. ARE-directed mRNA decay (degradation) is initiated by rapid removal of the poly-(A)tail, followed by degradation of the message corpus (see e.g. Chen C. Y et al., Trends Biochem. Sci. 1995, 20(11):465-70).

To date, several cytoplasmic mRNA-binding proteins have been identified to specifically interact with the ARE, whereas their binding shows either stabilizing, destabilizing or shuttling effects. Among these, the human ELAV (embryonic-lethal/abnormal-vision)-protein HuR (Hu-Antigen R) is proposed to be the central mRNA stabilizing protein involved in ARE-mediated mRNA degradation pathways (see e.g. Peng S. S. et al., EMBO J. 1998, 17(12):3461-70).

HuR (Hu-Antigen R) is a 36 kD protein of the RRM (RNA recognition motif)-superfamily which, in addition to stabilize short-lived mRNA by its ARE-binding activity in the 3'-UTR, has been shown to redistribute between the nucleus and the cytoplasm. Therefore, it is supposed to bind its cognate mRNAs in the nucleus and then escort them through the nuclear pore. It provides protection from degradation during and after export to the cytoplasm, thereby resulting in immediate up-regulation of the corresponding gene. The large family of AU-rich containing mRNAs associated with HuR-mediated regulation includes e.g. IL-3, c-fos, c-myc, GM-CSF (granulocyte/monocyte-colony stimulating factor), AT-R1 (angiotensin-receptor 1), Cox-2 (cyclooxygenase-2), IL-8 or TNF-α (see e.g. Hel Z. et al., Nucleic Acids Res. 1998, 26 (11): 2803-12).

The processes mediating up- and down regulation of immune mediators like IL-2, Cox-2 or TNF-α are key mechanisms in the immune response and represent an important target for immune intervention and anti-inflammatory therapies.

Despite the fact that a broad class of mRNAs use this generic type of regulatory element, previous studies have provided evidence that the ARE of a particular mRNA subsides a remarkably specific response to cell signaling. Hence, it appears to be feasible to identify mRNA-specific functional inhibitors by targeting individual AREs. This suggests that a great variety of disease relevant mediators, including proto-oncogenes, inflammatory cytokines and viral proteins, can be assayed based on the common regulatory principle of ARE- and HuR-mediated mRNA-stabilization and nuclear export.

The present invention provides a novel screening concept focused on the ERG-specific mRNA decay pathway mediated by the particular AREs and a protein, HuR, which antagonizes this degradation.

We have found that the interaction between the AREs in the 3'-UTRs of IL-2-(interleukin-2), TNF-α-(tumor necrosis factor-α), Cox-2-(cyclooxygenase-2) and other target-mRNAs and HuR can be determined according to a method of the present invention. The interaction of HuR with its cognate ARE-containing mRNA sequences represents an interesting target for potential anti-IL-2, anti-Cox-2, anti-TNF-α etc. directed immune intervention as a novel approach in targeting inflammatory diseases.

The assay concept of the present invention provides the possibility to identify compounds with an inhibitory effect on selected HuR-ARE target interactions. Moreover, it bears the potential of direct specificity crosschecks within the array of the corresponding mRNA-stability assays. This involves, in a first instance, inflammatory targets including AREs from TNF-α, IL-1β, IL-2, IL-8, Cox-2, IL-4 or AT-R1 but also offers the possibility to further expand the approach to other ARE-regulated target families. For instance, proto-oncogenes like c-myc, c-jun or c-fos are expected to be screenable. Hence, the assay concept of the present invention may serve as a basis for therapeutic intervention based on a novel mRNA-targeting approach.

The complex formation of an ARE-containing mRNA with an HuR protein in consequence induces the expression of various disease causing/mediating substances, e.g. inflammatory acting substances, e.g. cytokines, growth factors, proto-oncogenes or viral proteins. Agents which inhibit such a complex formation may thus prevent the expression of such substances, e.g. such agent may prevent (inhibit) or reduce the expression of inflammation mediating substance. Therefore such agents (inhibitors) may be used in the treatment of various diseases, e.g. diseases mediated by cytokines, growth factors, proto-oncogenes or viral proteins.

We have now found a soluble form of full-length HuR, which enables a simple and quick HTS procedure for screening of such agents.

In one aspect the present invention provides a method for identifying an agent that has an inhibitory effect on the complex-formation of an ARE-containing mRNA and an HuR protein comprising
(a) providing a soluble form of a HuR protein, with the proviso that a full-length HuR-glutathione-S-transferase fusion protein is excluded,
(b) providing an ARE-containing mRNA, (c) providing a candidate compound, wherein at least one of (a), (b) and (c) is labeled,
(d) mixing a) and b) in the presence of (c) and in the absence of (c) for a sufficient period of time so that a) and b) can form a complex,
(e) detecting the amount of complexes formed in step (d) and/or detect the non-complexed mRNA/protein species,
(f) comparing the amount of complexes formed and/or non-complexed mRNA/protein species found in the presence and in the absence of (c), and
(g) choosing an agent which has an influence on the complex formation detected in step (f).

A full-length HuR-glutathione-S-transferase fusion protein is disclosed in US2002/0165186, the content of which is introduced herein by reference.

A soluble form of a HuR protein means that said HuR protein shows no aggregation and precipitation, as controlled by e.g. size exclusion chromatography, in aqueous solvent, e.g. aqueous buffer of physiological pH at conditions, compatible with and suitable for e.g. spectroscopy, i.e. in the absence of micelle-forming detergents, glycerol etc., and at protein concentrations of >0.5 µM, preferably >5 µM. In contrast to that, wild-type full length HuR shows a high degree of aggregation and tendency for precipitation at these conditions, i.e. it is practically insoluble under analogous conditions. The concentration of protein used in an assay of the present invention depends on the binding affinity between a specific mRNA (fragment) and HuR, e.g. the protein concentration used in an assay of the present invention may be lower in case there is a high binding affinity between the two species or vice versa. Solvent include aqueous solvent, e.g. buffer solution, e.g. aqueous physiological buffer solution.

We have found a soluble form of a HuR protein, i.e. a specific fragment comprising the physiological binding activity of the full-length HuR to ARE-mRNA of SEQ ID NO: 3 or SEQ ID NO:4; and, even more surprisingly, a full-length HuR protein of SEQ ID NO: 1 or SEQ ID NO:2, wherein the carboxylic acid of only one single amino acid, i.e. the C-terminal amino acid K, is esterified compared to the wild-type. Preferably said carboxylic acid of the C-terminal amino add is esterified with an alkylmercapto-group, e.g. by use of 2-mercaptoethane-sulfonic acid or a salt thereof, e.g. sodium, to give the corresponding esterified HuR protein of SEQ ID NO: 1 or SEQ ID NO:2 in the form of a thioester.

In a further aspect the present invention provides a full length HuR protein of SEQ ID NO:1 or SEQ ID NO:2 (corresponding to SEQ ID NO:1, but without amino acid in position 1), wherein the C-terminal amino acid in position 326 is esterified, e.g. full length HuR protein of SEQ ID NO:1 or SEQ ID NO:2 in the form of a thioester.

In a further aspect the present invention provides an HuR protein fragment of SEQ ID NO:3 or SEQ ID NO:4.

An HuR protein fragment of SEQ ID NO:3 or SEQ ID NO: 4 comprises the mRNA recognition motifs 1 and 2, i.e. the amino acids 1-189 of SEQ ID NO:1 or the amino acids 2-189 of SEQ ID NO:1, comprising the quasi-physiological binding activity of the full-length HuR to ARE-mRNA. "Quasi-physiological" means a binding affinity under conditions of an assay of the present invention. A proof of binding affinities is given in e.g. Table 1.

In another aspect of the present invention the HuR protein is provided as a homogenous solution.

The ARE-containing mRNAs or mRNA fragments may be prepared by synthetic methods or in-vitro transcription. For synthetic preparation of mRNA fragments oligonucleotides are synthesized e.g. according, such as analogously, to a method as conventional, e.g. by use of (protected) phosphoramidites and coupling reagents in appropriate solvent. Longer fragments are preferably prepared by in-vitro transcription. Preferably the ARE-containing mRNA fragment has a length of 5 to 80 nucleotides.

We also found that HuR requires a minimum of 9 nucleotides for recognition. HuR binds with high affinity to a nonameric RNA sequence motif NNUUNNUUU, wherein U is uracil and N can be any one of the RNA nucleotides, adenine(A), cytosine (C), guanine (G) or uracil (U). This RNA sequence motif is the binding site for HuR. The Kd for binding of HuR to this motif is invariable (fundamental Kd) and is 0.97 nM+/−0.24.

In another aspect the present invention therefore provides an isolated RNA sequence motif, which is the binding site for HuR.

A candidate compound includes compound (libraries) from which its influence on the complex formation of an ARE-containing mRNA and an HuR protein according to the present invention may be expected, e.g. including (m)RNA fragments, DNA fragments, oligopeptides, polypeptides, proteins, antibodies, mimetics, small molecules, e.g. low molecular weight compounds (LMW's), preferably LMW.

An agent is one of the chosen candidate compounds, for which an influence on the complex-formation has been proven.

For detection purposes at least one of the substances (a), (b) or (c) bears a detectable label, e.g. an intrinsic labeled portion. Labeling may be carried out as appropriate, e.g. according, e.g. analogously, to a method as conventional, e.g. by chemical reaction of a reactive group in any of (a), (b) or (c) with a reactive group of the labeling substance. Such reactive groups include e.g. an amino acid residue, e.g. a cysteine residue, thioester, aldehyde, maleimide, maleimido-carboxylic acid, vinyl, haloalkylcarbonyl, hydroxysuccinimidylester. Preferably it is the mRNA fragment which is labeled, preferably it is fluorescently labeled.

Appropriate methods for the detection of complexes formed between the HuR protein and an ARE-containing mRNA and/or the non-complexed mRNA/protein species include fluorescence spectroscopy with a particular focus on applications with single molecule sensitivity e.g. Fluorescence Correlation Spectroscopy (FCS), Fluorescence Intensity Distribution Analysis (FIDA), or applications based on the determination of Fluorescence Anisotropy or Fluorescence Resonance Energy Transfer (FRET), e.g. as described in Kask P. et al, Biophys. J. (2000) 78 (4), 1703-1713.

In a preferred embodiment an assay of the present invention is performed by use of 2 dimensional-FIDA anisotropy analysis, wherein the fluorescence anisotropy of the complex between mRNA and HuR is determined at single molecule sensitivity by extension of the microscopic confocal detection setup to two polarisation channels.

In a further aspect the present invention provides a screening assay (kit) for identifying an agent that has an Inhibitory effect on the complex-formation of an ARE-containing mRNA and an HuR protein comprising the following components
a) a soluble form of a HuR protein, with the proviso that a full-length HuR-glutathione-S-transferase fusion protein is excluded,
b) an ARE-containing mRNA, and
c) optionally means for detection of the amount of the complexes formed between said ARE-containing mRNA and said HuR protein and/or the amount of non-complexed mRNA/protein species.

Said kit may further comprise a substantial component, e.g. including an appropriate environment of a sample to be tested and, e.g. appropriate means to determine the effect of a candidate compound in a sample to be tested.

In a further aspect the present invention provides a pharmaceutical composition comprising an agent identified by a method according to the present invention as an active ingredient in association with at least one pharmaceutical excipient.

For use as a pharmaceutical, an agent includes one or more agents, e.g. a combination of agents.

The pharmaceutical compositions according to the present invention may be used for the treatment of a disorder having an etiology associated with the production of a substance, e.g. an inflammatory acting (causing/enhancing) substance, selected from the group consisting of cytokine, growth factor, proto-oncogene or viral protein. Preferably said substance is selected from the group consisting of IL-1, IL-2, IL-3, IL-4, IL-8, GM-CSF, TNF-α, VEGF, AT-R1, Cox-2, c-fos and c-myc. Treatment includes treatment and prophylaxis.

In the following examples all temperatures are given in degree Celcius and are uncorrected. The following ABBREVIATIONS are used:
AREs AU-rich elements
CBD chitin binding domain
CPG controlled pore glass
DTT dithiothreitol
DMSO dimethylsulfoxide
EDTA ethylenediaminetetraacidic acid
ERGs early-response genes
HRP horse radish peroxidase
Hu-antigens antigens present in patients with the Hu-Syndrome (e.g. HuB, HuC, HuD and HuR)
Hu-Syndrome paraneoplastic encephalomyelitis sensory neuropathy
IMPACT™-CN System Intein mediated purification with an affinity chitin-binding tag
IPTG isopropyl-thio-β-D galactopyranoside
LB-Amp 200 LB medium containing Ampicillin at 200 μg/ml
LB medium Luria Bertani broth medium
(Na)-2-MESNA 2-mercapto ethane sulfonic acid (sodium salt)
nt nucleotide
ORN oligoribonucleotide
PVDF polyvinylidene fluoride
RP-HPLC reversed phase-high performance liquid chromatography
rpm rotations per minute
RRM RNA recognition motif
RT room temperature
TAE buffer Tris-acetate-EDTA buffer
TBAF tetrabutylammonium fluoride
TCA trichloro acid
tBdMS tert.butyldimethyl-silyl
TEAAc triethylammonium acetate
TFA trifluoroacetic acid
TLC thin layer chromatography
TMR carboxytetramethylrhodamine
TOM triisopropyloxymethyl
UTR untranslated region

EXAMPLE 1

Soluble Form of a Full-Length Human HuR (=sfl-HuR)

Preparation of recombinant full length human HuR encompassing amino acids 1-326 (=SEQ ID NO: 1) or with missing amino acid M in position 1 (=SEQ ID NO:2):

MSNGYEDHMAEDCRGDIGRTNLIVNYLPQNMTQDELRSLFSSIGEVESAK

LIRDKVAGHSLGYGFVNYVTAKDAERAINTLNGLRLQSKTIKVSYARPSS

EVIKDANLYISGLPRTMTQKDVEDMFSRFGRIINSRVLVDQTTGLSRGVA

FIRFDKRSEAEEAITSFNGHKPPGSSEPIAVKFAANPNQNKNVALLSQLY

HSPARRFGGPVHHQAQRFRFSPMGVDHMSGLSGVNVPGNASSGWCIFIYN

LGQDADEGILWQMFGPFGAVTNVKVIRDFNTNKCKGFGFVTMTNYEEAAM

AIASLNGYRLGDKILQVSFKTNKSHK$_{326}$ using the IMPACT™-CN System [New England Biolabs] is performed as follows.

a) Cloning

Full-length human HuR is PCR-amplified from cDNA libraries prepared from, both, activated human T-lymphocytes as well as human monocyte-derived dendritic cells, and cloned directionally into the NdeI and SapI sites of the vectors pTXB1 and pTYB1 [New England Biolabs], allowing C-terminal fusion with the intein-CBD tag without insertion of any additional amino acid.

cDNA cDNA of poly-(A)+ RNA from activated human T-lymphocytes and of poly(A)+ RNA from LPS-stimulated monocyte-derived dendritic cells is prepared from both RNA sources using the Thermoscript™RT-PCR System [GIBCO/LIFE TECHNOLOGIES]. The resulting cDNA is used for PCR amplification of human HuR.

PCR

Primers flanking the complete coding sequence (CDS) (encompassing amino acids 1-326) are designed with overhangs containing the appropriate restriction sites to clone directionally into the NdeI and SapI restriction sites of the vectors pTXB1 and pTYB1.

```
Forward primer:
5'-GGAGGAGGAGGCATATGTCTAATGGTTATGAAGACCACAT-3'

Reverse primer:
5'-AAATAATGCTCTTCCGCATTTGTGGGACTTGTTGGTTTTG-3'
```

Nucleotides in bold indicate restriction enzyme sites added to the PCR product for directional cloning.

For each cDNA source, 7 identical PCR reactions are carried out using standard PCR conditions. The PCR reaction products are purified by preparative agarose gel electrophoresis on a 0.8% (w/v) agarose gel (15×15×0.8 cm) in TAE buffer containing 10 μg/ml ethidiumbromide at 80 V (constant voltage) for 90 min. Bands are excised with a sterile scalpel on the Dark Reader under transillumination at 480 nm.

The samples are extracted from the agarose gel slices using the NucleoSpin Extract 2in1 Kit [Machery&Nagel] according to the manufacturer's protocol.

Sequencing

After PCR, the sequence of the amplificates is verified by automated DNA sequencing. From each cDNA source, the DNA-sequence of two PCR samples is analysed. The sequencing reactions are performed using the ABI PRISM™ BigDye™ Terminator Cycle Sequencing Ready Reaction Kit [PE APPLIED BIOSYSTEMS], according to the manufacturer's protocol. Capilary electrophoresis is carried out on the ABI™ PRISM 310 GENETIC ANALYZER [PE APPLIED BIOSYSTEMS] following a standard protocol. Data are processed with the ABI™ PRISM 310 Software[PE APPLIED BIOSYSTEMS].

Restriction Enzyme Digestion

Following double-digestion of PCR products from both cDNA sources and of the vectors pTXB1 and pTYB1 with NdeI and SapI, vector DNA and PCR products are separated by preparative agarose SGE (slab gel electrophoresis). Bands of the appropriate size (6458 bp for pTXB1/NdeI-SapI; 7426 bp for pTYB1/NdeI-SapI; 985 bp for PCR products) are excised with a sterile scalpel under transillumination on the Dark Reader (480 nm) and extracted from the gel using the QIAquick Gel Extraction Kit [QIAGEN] following the manufacturer's protocol. The eluted DNA is quantified by measuring the UV-Absorption at 260 nm on a LKB Biochrom II Spectrophotometer, using 50 microliter UV-silica cells [LKB Biochrom Ultrospec UV-silica cells, P/N 4001-088].

Ligation

NdeI/SapI digested PCR products from both cDNA sources are ligated into the vectors pTXB1 and pTYB1 in both, 1:1 and 3:1 (insert:vector) molar ratios with T4 DNA Ligase, to yield the plasmids pTXB1/HuR and pTYB1/HuR, respectively.

Transformation

Home-made $CaCl_2$ competent cells of E. coli ER2566 are transformed with the plasmids pTXB1/HuR and pTYB1/HuR from the ligation reactions (with HuR inserts from both cDNA sources), using slightly modified conditions from a standard protocol for heat-shock transformation of chemically competent cells. The transformed bacteria are plated onto LB-Amp plates and colonies are grown over night at 37°. Single clones are picked and grown in liquid culture to late log-phase. The recombinant plasmid DNA is isolated from harvested bacterial cells using the QIAprep Spin Miniprep Kit [QIAGEN] following the manufacturer's protocol and checked for the presence of the correct insert size by restriction enzyme digestion with NdeI vs. double-digestion with NdeI and PstI (for pTXB1/HuR) or NdeI and KpnI (for pTYB1/HuR), respectively.

The sequences of all resulting recombinant plasmids are verified by automated DNA-sequencing, as specified above. DNA-sequences are generated using primers complementary to consensus sequences upstream of NdeI and downstream of SapI sites with binding sites within the vector DNA.

b) Expression and Purification

Expression of the cloned HuR-Intein-CBD fusion protein is induced by addition of 1 mM IPTG to a bacterial culture grown to late-logarithmic phase in LB broth medium and allowed to proceed for 6 hours at 28°. The bacterial cells are lysed by successive freezing/thawing cycles in a buffer of 20 mM Tris/Cl pH 8.0, 800 mM NaCl, 1 mM EDTA and 0.2% Pluronic F-127 (Molecular Probes). After DNA digestion, the bacterial lysates are cleared by ultracentrifugation and the fusion protein is captured onto chitin agarose beads (New England Biolabs) via the CBD. After extensive washing of the beads with lysis buffer, the recombinant protein is recovered by thiol-induced on-column self-splicing of the intein tag by addition of Na-2-MESNA to a final concentration of 50 mM and incubation for 12 hours at 4°. Any co-eluted intein tag and un-cleaved fusion protein are removed from the eluate in a second, subtractive affinity step. Finally, the protein is transferred into the appropriate storage buffer by elution through a gel filtration column (DG-10, Bio-Rad) previously equilibrated with the target buffer (25 mM $Na_2HPO_4$/$NaH_2PO_4$ pH 7.2, 800 mM NaCl, 0.2% (w/v) Pluronic F-127), shock-frozen in small aliquots in liquid nitrogen and stored at −80°. A full-length HuR protein which is esterified by Na-2-MESNA is obtained as a thioester. The obtained thioester shows no aggregation and precipitation (as controlled by e.g. size exclusion chromatography and/or UV-spectroscopy) in aqueous buffer of physiological pH at e.g. spectroscopy-compatible conditions and at concentrations of >0.5 µM, preferably >5µM.

c) Characterisation

The quality of the purified protein is controlled by denaturing SDS-PAGE, UV-spectroscopy, analytical Size Exclusion Chromatography, RP-HPLC analysis, LC/ESI-MS analysis and CD-spectroscopy, following standard protocols as described in example 2. At the described conditions, full-length HuR is soluble without the need for a hydrophilic fusion tag, like e.g. gluthatione-S-transferase. Results from UV-spectroscopy, showing no absorbance at >330 nm, and analytical size exclusion chromatography, where HuR elutes as a single peak with a maximum at 24.2 kD, provide evidence that no higher aggregation states of the protein are present at the given buffer concentrations.

EXAMPLE 2

HuR—Variant (HuR12) Encompassing the First Two RRMs of SEQ ID NO:1 Only (aa1-189 of SEQ ID NO:1=SEQ ID NO: 3) or aa2-189 of SEQ ID NO:1 (=SEQ ID NO:4)

A shorter soluble variant of human HuR encompassing the amino acids as described above is prepared using the IMPACT-TWIN System [New England Biolabs] by directional cloning into the restriction sites NdeI and SapI. In recent studies, these first two fragments are identified to be crucial and sufficient for efficient RNA binding, and comparable findings concerning related proteins (HuD, Sxl) lead to the conclusion that most likely, this shorter construct will keep enough specificity in ligand binding. Soluble recombinant protein is prepared from bacterial culture.

a) Cloning

Cloning is carried out as described in example 1 but primers flanking the complete coding sequence of human HuR from amino acid 1-189 (in the following referred to as HuR12) are designed accordingly.

b) Expression

E. coli ER2566—pTWIN1/HuR12 is used as expression system for the large-scale preparation of recombinant human HuR12. Fermentation is carried out as described in example 1. Upon induction of expression by IPTG, SDS-PAGE analysis of crude bacterial cell lysates revealed an emerging protein band at ~48 kD, corresponding to the expected size of the cloned HuR12-Mxe-Intein-CBD fusion protein.

c) Purification

Affinity chromatography is carried out as described in example 1.

Preparative HPLC-Purification of HuR12

The solution eluted from the second chitin column is further purified by preparative RP-HPLC. Briefly, total protein concentration in the solution is assessed using a Bradford Protein Assay [Bio-Rad] according to the manufacturer's protocol. In each preparative run, a volume corresponding to 1 to 5 mg protein is injected onto a DeltaPak™ C4, 15 µm, 300 Å, 250×10 mm RP-HPLC column [WATERS]. Elution is performed with a linear gradient from 100% A (5% (v/v) $CH_3CN$/$H_2O$, 0.1% TFA) to 100% B (95% (v/v) $CH_3CN$/

H₂O, 0.1% TFA) within 50 minutes at a constant flow of 10 ml/minute. Detection is performed by measuring UV-absorbance at 230 nm and fluorescence at $\lambda_{ex}$=280 nm/$\lambda_{em}$=340 nm. HuR12 typically eluted at ~60% B (corresponding to ~59% (v/v) CH₃CN). Fractions à 3 ml are collected, analyzed by denaturing, non-reducing SDS-PAGE and HuR12-containing fractions are pooled. The solution is finally shell-frozen in liquid N₂ and the protein is lyophilized for 36 hours at −59°, 0.005 mbar. The flask containing lyophilized HuR12 is flushed with Argon and stored for subsequent purification steps at −20°.

Refolding by Ion-Exchange Chromatography

Lyophilized HuR12 (theoretical pI=7.84) is refolded on an Ion-Exchange column. Briefly, for each chromatographic run, 1-1.5 mg lyophilized HuR12 is weighed under Argon, dissolved in a 50 mM NaH₂PO₃/Na₂HPO₃ buffer pH 5.50, containing 8M urea and loaded directly onto the bed of a 10 mm i.d.×90 mm column packed with S-Sepharose FF [AMERSHAM PHARMACIA BIOTECH]. After attaching the column to a LKB-LCC 500 instrument, the protein is eluted with a gradient of increasing NaCl concentration. During the gradient, fractions of 1 ml are collected. Aliquots are subjected to denaturing, non-reducing SDS-PAGE and protein bands are visualized by silver staining. HuR12 typically eluted between concentrations of 250 mM and 350 mM NaCl (max. at 285 mM NaCl). Fractions containing HuR12 are pooled, concentrated by centrifugation in AMICON CENTRIPREPS[YM-3, MWCO=3000 Da] by a factor of 5, dialyzed against the storage buffer (25 mM NaH₂PO₃/Na₂HPO₃, 300 mM NaCl, 1 mM EDTA, pH 6.00), shock-frozen in little droplets in liquid nitrogen and stored at −80°.

d) Biochemical Characterisation

Analytical Size Exclusion Chromatography

30 μg of purified HuR12 are injected onto a Zorbax DuPont GF-250, 9.4 mm i.d.×25 cm column [HP, P/N 884973901] and isocratically eluted with storage buffer (25 mM NaH₂PO₃/Na₂HPO₃, 300 mM NaCl, 1 mM EDTA, pH 6.00) at a constant flow of 1 ml minute. Detection is performed by measuring UV-Absorption at 280 nm and fluorescence at $\lambda_{ex}$=280 nm and $\lambda_{em}$=340 nm (Gain=10, Attenuation=8) with the two detectors arranged serially. The retention time of the sample is compared to the chromatogram obtained from a size standard at the same conditions. HuR12 elutes as a single peak with a peak maximum at 20.41 kD (base width=8.33 kD-36.14 kD), which provides evidence that no higher aggregation states of the protein have to be supposed at the given buffer concentrations.

N-Terminal Sequencing 500 pmol of lyophilized HuR12 are subjected to N-terminal Edman Sequence Analysis (Protein Sequencer HP-G1000A). The sample shows a homogeneous N-terminus yielding the expected amino acid sequence (SNGYEDHMAEDCRGDIGRTN), but quantitatively missing the N-terminal Met. The purity of the sample calculated from sequence analysis is >97%.

Mass Spectrometry 500 ng of lyophilized HuR12 are subjected to LC-ESI/TOF (Liquid Chromatography-Electrospray Ionization/Time-of-Flight) Mass Spectrometry. The MS-Spectrum yields four main peaks:

A . . . 20849.5 Da (<5%)
B . . . 20974.3 Da,=A+124.9 Da (>95%)

A corresponds exactly to the expected mass of the amino acid sequence SEQ ID NO:2 $S_{position2}$NGYEDHMAEDCRGDIGRTNLIVNYLPQNMTQDELRSLFSSIGEVESAKLIRDKVAGHSLGYGFVNYVTAKDAERAINTLNGLRLQSKTIKVSYARPSSEVIKDANLYISGLPRTMTQKDVEDMFSRFGRIINSRVLVDQTTGLSRGVAFIRFDKRSEAEEAITSFNGHKPPGSSEPITVKFAANPNQ$_{189}$, which accounts for the N-terminus missing the Met (as revealed by N-terminal sequencing). The mass of B corresponds to the same amino acid sequence but carrying a C-terminal 2-ME-SNA-thioester.

Western Blotting 500 ng of the purified protein are subjected to denaturing, reducing SDS-PAGE followed by transferring the protein bands onto a PVDF membrane using standard semi-dry blotting conditions. Protein bands are detected using mouse monoclonal anti-HuR 19F12 (raised against an N-terminal peptide, MOLECULAR PROBES) as primary antibody, HRP-linked goat-anti-mouse IgG (H+L) [PIERCE] as secondary antibody and visualized after incubation with HRP-substrate [ECL™ Western Blotting Detection Kit, AMERSHAM PHARMACIA BIOTECH] and exposure of the blot to X-ray films. The developed films reveal a strong signal of the anti-HuR antibody at a size corresponding to the band of HuR12 (21 kD) and a weak signal at a band corresponding to approximately 42 kD, which indicates the presence of HuR12-dimer. An even weaker signal is detected at a size of ~70 kD, further indicating a minor amount of HuR12-trimer in the sample.

CD-Spectroscopy

The folding of the protein after the purification procedure as well as following fluorescent labeling is monitored by CD-Spectroscopy. The data collected indicate that HuR12 prepared as described above is folded and shows a secondary structure with beta-sheet and alpha-helical contents (~30%). An additional series of experiments provides evidence that upon RNA-binding the protein secondary structure does not subside any considerable change, whereas remarkable changes in the RNA secondary structure take place upon HuR12 binding. The obtained protein shows no aggregation and precipitation, as e.g. controlled by size exclusion chromatography and/or UV-spectroscopy, in aqueous buffer of physiological pH at e.g. spectroscopy-compatible conditions and at concentrations >100 μM.

EXAMPLE 3

Fluorescence Labeling of HuR12

For site-specific fluorescent labeling of the prepared protein HuR12 several approaches, as described already earlier, can be followed. To give one example, the presence of only one cysteine residue (position 13) in the shorter variant of HuR is ideally suited for site-specific labeling by conjugation of the thiol-group to the double bond of a maleimide-activated fluorescent dye. 5-carboxy-TMR-maleimide as one of the most stable and best characterized dyes is selected and attached to HuR12.

EXAMPLE 4

Preparation of mRNA Fragments

The specific process of mRNA stabilization associated with HuR-mRNA binding is controlled by cis-acting sequence elements in the 3'-UTR of the messages targeted for degradation. The responsible elements are sequences rich in A and U (termed AU-rich elements, ARE), essentially characterized by the presence of several repeats of the pentamer AUUUA. Characteristically, these are clustered within a region rich in U, often in the form of overlapping nonamers UUAUUUAUU. These elements range from 9 to about 100 nts in size with a typical length of ~30 nts—a length ideally suited for chemical synthesis. However, there exists evidence that the in-vivo destabilizing potential of the ARE alone is remarkably weaker than that of the same ARE embedded within the environment of the entire 3'-UTR. Therefore, not only the ARE itself, but also fragments of increasing size around the AREs of the messages of interest (e.g. IL-2, TNF-alpha, IL-1, Cox-2) as well as, whenever possible, full-length 3'-UTRs will be applicable in the present assay concept.

Since enzymatic methods do not allow the introduction of single labels at specific positions within an mRNA sequence, the method of choice for all fragments <50-70 nts is total chemical synthesis on an Applied Biosystem 394A synthesizer. Chemical synthesis is performed with nt phosphoramidites with two different classes of 2'-protecting groups, referencing to and adopting protocols from e.g. Auer M. et al., in: Schroeder & R Wallis M, editors. *RNA-Binding Antibiotics: Molecular Biology Intelligence Unit 13. Georgetown, Tex.: Landes Bioscience,* 2001:164-180. An aminolinker is introduced during the synthesis in order to allow the coupling with a range of different dyes in a post-synthesis reaction. The linker is e.g. Introduced at the 5'-terminus of all synthesized fragments.

Synthesized ORNs are deprotected and purified by preparative polyacrylamide gel electrophoresis (PAGE) followed by extraction and electroelution from excised gel slices. Concentrations are determined by measuring absorption at 260 nm. The purity of the fragments is controlled by analytical HPLC.

a) Chemical Synthesis

RNA ORNs are synthetized with 5'-O-dimethoxytrityl-2'O-tBdMS-protected β-cyanoethyl-(N,N-diisopropyl-)phosphoramidites- or 5'-O-dimethoxytrityl-2'O-TOM-protected nt phosphoramidite solutions [0.1 M in anhydrous $CH_3CN$] and 2'-tBDMS- or 2'-TOM-protected nts, respectively, immobilized on CPG on an Applied Biosystem 394A synthesizer at the 1 μmol scale, adopting published procedures [e.g. Chaix C. et al., *Nucleic Acids Symp Ser.* 1989 (21) 45-6; Scaringe S. A. et al., *Nucleic Acids Res.* 1990 Sep. 25; 18(18):5433-41] and manufacturer's protocols. The coupling reagents are added in two consecutive portions with a 15 seconds waiting step. Activation of the phosphoramidites in the coupling steps is performed with tetrazole (0.5 M in anhydrous $CH_3CN$). During the 11 minutes (for 2'-tBdMS-protected nt-phosphoramidites) or 7 minutes (for 2'-TOM-protected nt-phosphoramidites) coupling period, respectively, the CPG support is periodically agitated by 0.1 seconds "up and down" pulses of the reagent solution. Capping with acetic anhydride/THF is performed for 20 seconds, oxidation with $I_2$/THF/pyridine/$H_2O$ for 1 minute, washing steps with $CH_3CN$ for 40 seconds. Dimethoxytrityl deprotection is done with 3% (w/v) TCA/$CH_2Cl_2$ delivered in four 40 seconds portions and a total reaction time of 5 minutes. 6-(4-Monomethoxytritylamino)hexyl-(2-cyanoethyl)-(N,N-diisopropyl) phosphoramidite is manually coupled at the 5' position of the growing oligonucleotide for 15 minutes by luer syringe delivery, using 11 μmoles of reagent directly dissolved in 200 μl of the activating solution under argon atmosphere. The dissolved reagent is drawn into a dry syringe and, after removal of the needle, pushed through the cartridge, closing the second luer connection with another syringe. During the 15 minutes coupling time, the solution is periodically agitated by synchronous agitation of the two syringes. The remaining steps of the synthesis cycle are done on the instrument. The efficiency of the aminolinker incorporation is assessed based on the colour intensity of the collected detritylation solution.

b) Purification of Synthesized mRNA

Cleavage from the Support, Base and Phosphate Deprotection

The crude RNA products from 1.0 or 0.5 μmol scale synthesis are cleaved from the CPG-support and base- and phosphate-deprotected with saturated ethanolic $NH_3$. After incubation for 17 hours at 40°, the supernatant is collected. The CPG is additionally washed three times with ethanol, followed by washings with ethanol/$H_2O$ (1:1) and $H_2O$. The washing solutions are combined with the cleavage solutions and solvent is evaporated.

2' Desilylation

For 2' deprotection of the crude ORNs, dried products are dissolved in 1.8 ml of a 1.1 M TBAF/THF solution and incubated on the vortex mixer at RT for at least 15 hours. The reaction is quenched by adding 400 μl of a 0.5 M $NH_4Ac$-solution and incubation on ice for 10 minutes. The solution is diluted to a final concentration of 50% (v/v) by addition of 1.4 ml of $H_2O$ and partially evaporated to ~2.5 ml. The solution is desalted, ORN containing fractions, as determined by measuring the absorption at 260 nm, are combined and solvent is evaporated.

Page-Purification of the Crude RNA Products

Dried fractions of the RNA samples are dissolved in $H_2O$, precipitated with ethanol and pelleted by centrifugation. The pellet is dried, dissolved in $H_2O$ and diluted 1:1 with gel loading buffer (95% (v/v) de-ionized formamide, 0.5 mM EDTA, 0.025% (w/v) xylene cynol blue, 0.025% (w/v) bromphenol blue, 0.025% (w/v) SDS). Prior to electrophoresis, the RNA is denatured for 2 minutes at 85° and immediately cooled on ice. The samples are purified by electrophoresis on denaturing 12% polyacrylamide gels (6M urea, 12% (w/v) acrylamide/bisacrylamide (40:1), Tris-borate-EDTA buffer; 400×200×1.5 mm). Electrophoresis is performed at 45 W (constant power) for 4 hours or until the bromphenol blue has migrated ~⅘ of the distance to the bottom. After electrophoresis, the gel is removed from the plates and covered in Saran wrap. The bands are visualized by UV shadowing on fluorescent TLC plates at 254 nm (hand held UV lamp) and photographed with Polaroid PoloPan 52 Iso400 (Kodak UV Wratten filter, f.3.5) for 20 seconds.

Recovery of RNA Fragments from Polyacrylamide Gels

Gel slices with the main products are cut and the RNA is extracted from the polyacrylamide gel slices prior to electroelution by cutting them into small pieces and incubating them with 50 mM $NH_4Ac$ for at least 9 hours at RT. Additionally, any remaining RNA in the gel is recovered by electroelution in Schleicher and Schuell Elutraps 100 for at least 3×1 hr 30 minutes at 200 V (constant voltage) in TAE buffer. The solution is desalted, ORN containing fractions, as determined by measuring the UV-absorption at 260 nm, are combined and solvent is evaporated.

c) Characterization

HPLC analysis is performed on a Beckman System Gold Instrument (Beckman System Gold Programable Solvent Module) equipped with a UV detection device (Beckman System Gold Programable Detection Mode) and a fluorescence detector (Waters™ 471 Scanning Fluorescence Detector). Data analysis is performed with the Beckman System Gold MDQ software. Chromatography is performed on a protein/peptide purification column i.e. VYDAC™ Protein & Peptide Column (4.6×250 mm, 300 Å-C18-5μ) with a washing step of 100% solvent A (0.1 M TEAAc, pH 6.5/CH$_3$CN, 95:5) for 5 minutes and elution with a continues gradient from 100% solvent A to 100% solvent B [A (0.1 M TEAAc, pH 6.5/CH$_3$CN, 50:50] in 45 minutes at RT. For analytical runs, 1.5 to 30 μg of purified RNA is injected after denaturation for 2 minutes at 85° and incubation for 5 minutes on ice. Based on this procedure, 29 different fragments of 5-58 nts in length selected from AU-rich elements of human IL-1, IL-2, IL-4, IL-8, Cox-2, TNF-α, AT-R1 as well as various strategically designed comparative sequences are synthesized. An amino-C6 modifier [Glen Research] is incorporated into the 5' terminus of 25 out of the 29 synthesized sequences. This modification allows to introduce a succinimidylester-activated fluorescent dye (see example 6).

EXAMPLE 5

Performance of the Assay(s)

Titration of fluorescently labeled RNA fragments corresponding to the AREs of, for example, IL-2, IL-4, IL-8, Cox-2, IL-1β or TNF-α (5'-terminally labeled with 5'-carboxy-TMR and 33, 58, 26, 35, 33 and 34 nts in length, respectively), against increasing concentrations of a soluble form of recombinant full-length HuR or HuR12 is performed. The predicted increase in size and hence, in anisotropy for the free ORNs (Mr about 6000-12000 Da) upon complexation with HuR (Mr ~360912) or HuR12 (Mr ~20974) suggests that the change in the anisotropy signal is sufficient to be detected with the requested precision.

As shown in TABLE 1, data clearly indicate a substantial and reproducible variability in the protein's affinity for the individual AREs. In vitro, individual AU rich elements are bound to HuR with different affinity, although they are derived from mRNA targets which are known to be associated with HuR-mediated regulation. This fragment selectivity is retained when the third RRM as well as the hinge region are missing as is the case for HuR12. This suggests a recognition mechanism that is solely mediated by the first two RRMs, which is in good consistence with observations from previous studies. However, the full length protein binds to all fragments with a higher affinity. The Kd is lower by an almost constant factor of 50. In contrast, the low affinity fragments (Kd for HuR12>1 μM) are no longer recognized by the full length protein at all (see TABLE 1). This suggests a further role of the third RRM, namely to strengthen the RNA-complexation and to reduce the tolerance towards unspecific RNA ligands, leading to an increased level of specificity.

The affinity of HuR for the TNF-α ARE (Kd=0.12 nM+/−0.02) is significantly higher than for example for the Cox-2 ARE (Kd=13.63 nM+/−1.07). This effect is particularly surprising as the sequence is not strikingly different, although not identical (see TABLE 1). We conclude that there is indeed a sequence dependent and highly specific mechanism responsible for HuR binding. Consequently, we conclude that the recognition is further not based on general affinity to single AUUUA elements, but that spacing, number and sequence surrounding this pentanucleotide core is of substantial importance. As the experiments are performed with full-length HuR and HuR12, the shortened variant of full-length HuR, we further reason that the specificity of HuR-mediated mRNA stabilization is not only attributed to the third RRM. It appears probable that the specificity of HuR-mediated mRNA stabilization is based on a combination of two effects: the third domain of HuR is responsible for specific interaction with other regulatory proteins, whereas the first two domains display sequence specificity or, at least, selectivity. This finally suggests the possible identification of inhibitors specific for individual HuR-ARE targets or target families already at the level of RNA recognition.

TABLE 1

ARE sequences and K$_d$ values determined in the described 2D-FIDA-r assay

| | Sequence | K$_d$ sfl-HuR in nM +/− St. dev. | K$_d$ HuR12 in nM +/− St. dev. |
|---|---|---|---|
| TNF-α | AUUAUUUAUUAUUUAUUU AUUAUUUAUUUAUUUA | 0.35 +/− 0.06 | 21.45 +/− 2.95 |
| IL-2 | UAUUUAUUUAAAUAUUUA AAUUUUAUAUUUAUU | 9.5 +/− 1.34 | 497.89 +/− 36.02 |
| IL-1β | UAUUUAUUUAUUUAUUUG UUUGUUUGUUUUAUU | 0.12 +/− 0.02 | 18.36 +/− 2.01 |
| IL-4 | AUUUUAAUUUAUGAGUUU UUGAUAGCUUUAUUUUUU AAGUAUUUAUAUAUUUAU AA | 3.21 +/− 0.35 | 154.41 +/− 22.83 |
| IL-8 | UAUUUAUUAUUUAUGUAU UUAUUUAA | 1.09 +/− 0.16 | 42.88 +/− 5.73 |
| Cox-2 (2) | UAUUAAUUUAAUUAUUUA AUAAUAUUUAUAUUAAA | 13.63 +/− 1.07 | 229.48 +/− 19.17 |
| (AUUU)$_4$A | AUUUAUUUAUUUAUUUA | 2.09 +/− 0.16 | 125.91 +/− 16.34 |
| (AUUU)$_5$A | AUUUAUUUAUUUAUUUAU UUA | 0.4 +/− 0.05 | 23.47 +/− 8.92 |

TABLE 1-continued

ARE sequences and K$_d$ values determined in the described 2D-FIDA-r assay

| | Sequence | K$_d$ sfl-HuR in nM +/− St. dev. | K$_d$ HuR12 in nM +/− St. dev. |
|---|---|---|---|
| (AUU)$_5$A | AUUAUUAUUAUUAUUA | n.b. | 1592.79 +/− 281.29 |
| irrelevant seq. | UAGAGUUCAUCGCAAUUGCAC | n.b. | n.b. | n.b. = no binding; St. dev. = standard deviation; sfl-HuR = soluble form of full length HuR

EXAMPLE 6

Fluorescence Labeling of ORNs

Labeling Reaction

Fluorescent dyes can be attached to the amino group introduced with the 5'-terminal linker by a standard reaction of primary amines with succinimidylester-activated molecules leading to the formation of a stable carboxamide. For this purpose, 5-10 nmol of purified RNA in max. 20 µl of H$_2$O is mixed with a 0.5 M stock solution of Na$_2$CO$_3$/NaHCO$_3$ buffer, pH 9.0, to a final buffer concentration of 150-300 mM. To give one example, TMR-NHS (5-carboxy-TMR-N-hydroxy-succinimidylester) is dissolved in anhydrous DMSO under Argon atmosphere and added to the RNA to a 25-fold molar excess, whereas the final DMSO concentration in the labeling reaction does not exceed 30% (v/v). Incubation is carried out for at least 2 hours at RT on the vortex-mixer, protected from light. Unreacted dye is hydrolyzed by addition of 1.5 M NH$_2$OH—HCl to a 50-fold molar excess and incubation for 30 minutes at RT on the vortex-mixer, protected from light.

Purification of Labeled RNA

After labeling, the RNA is separated from the free dye, fractions à 0.5 ml are collected and analysed by RP-HPLC as described above. Detection of labeled and unlabeled RNA and of the free dye is performed by measuring UV-absorption at 260 nm as well as fluorescence at $\lambda_{ex}$=541 nm, $\lambda_{ex}$=567 nm, corresponding to the excitation/emission maxima of TMR. Fractions containing RNA are further purified by preparative RP-HPLC at analogous conditions. Peaks of both, labeled and unlabeled RNA, are collected separately in pointed flasks and the volume of the solutions is reduced by evaporation on the Rotavapor. The solutions are transferred quantitatively to Eppendorf tubes and co-evaporated 5-7 times with H$_2$O ethanol to remove any remaining TEAAc. The dried RNA is dissolved in H$_2$O to a concentration of 20-50 µM and stored at −20° for further use.

EXAMPLE 7

RNA-Fragments Prepared by In-Vitro Transcription a) Preparation of the DNA Template For the biochemical preparation of 3'-UTR fragments of mRNAs which are too long to be chemically synthesized, in the first step, a recombinant plasmid containing the full-length 3'-UTR (or the region of interest) of each mRNA needs to be available. This plasmid subsequently serves as a template for in-vitro transcription of selected sub-fragments. Templates for the full-length 3'-UTR of human IL-2, IL-1β and the first 600 bp from the 3'-UTR of TNF-β are prepared.

TNF-α: A recombinant plasmid containing the complete coding sequence as well as the first 600 base pairs of the 3'-UTR of TNF-α is purchased from ATCC (American Type Culture Collection, #39918, construct: pAW711).

IL-2: A recombinant plasmid containing the full-length 3'-UTR of human IL-2 is prepared following an analogous procedure as described in example 1.

Briefly, the full length 3'-UTR of human IL-2 is PCR amplified from a cDNA library prepared from human T-lymphocytes with primers designed with overhangs containing the appropriate restriction sites to clone directionally into the KpnI and SpeI restriction sites of the vector LITMUS28 [New England Biolabs]. The PCR-amplificates and the vector DNA are double digested with the restriction enzymes KpnI and SpeI, ligated with T4-DNA Ligase and transformed using a standard heat-shock protocol into CaCl$_2$-competent E. coli INVαF'. After plating onto selective LB-Agar plates, single colonies containing recombinant plasmid DNA (as determined by blue-white selection) are picked and grown to late log-phase in liquid LB-Amp medium. The sequences of the isolated recombinant plasmids from three single clones are verified by automated DNA sequencing as specified above and could be aligned to 100% identity to the 3'-UTR of human IL-2 (GenBank Ac. No. U25676).

In-vitro Transcription:

To give one example, a transcript corresponding to the first 697 nts of TNF-α 3'-UTR is prepared by in-vitro transcription as follows: A PCR-product is prepared from primers flanking nts 1-697 of the 3'-UTR of TNF-α, incorporating the promoter sequence for T7-RNA polymerase at the 5' terminus. A run-off transcript is subsequently prepared using the MEGASCRIPT T7-IN-VITRO TRANSCRIPTION KIT [AMBION], following the manufacturer's protocol. After transcription, the DNA template is digested with RNAse-free DNAse I and the mixture is further purified by repeated extraction steps with acidic phenol-chloroform. RNA is precipitated with ethanol, dissolved in nuclease free H$_2$O and stored at −80°. The product is further analyzed by PAGE with ethidiumbromide staining for visualization, revealing a single band migrating at the expected molecular weight. Additional RP-HPLC analysis with UV-detection at 260 nm (see example 2) accordingly shows a single peak for the RNA transcript.

EXAMPLE 8

Deduction of the HuR Binding Site

Based on our previous observation that polyU is bound by HuR with high affinity, the effect of elongation of U$_8$ was tested. Individual RNA fragments are synthesized and the affinities (given as Kd values) to full length HuR are determined (see TABLE 2). While the simplest variant of U$_8$ motif (fragment No. 1) is not recognized by HuR, an elongation by one nucleotide to U₉ (fragment No. 2) shows a sufficient high binding. An influence of the fluorescent dye is excluded by competition experiments with unlabeled RNA fragments. The 9mer fragment (fragment No. 3) contains the HuD motif and an additional nucleotide 3' terminally but is not bound by HuR. The high affinity binding to fragment No. 4 however indicates that non-U nucleotides are tolerated within HuR binding motif, but at certain positions only. We have found that 9 nucleotides are sufficient for binding of HuR and four different 9mer frames within (AUUU)₃A were tested (see fragments No 4a) to 4d) in bold). The exclusive recognition of fragment 4b by HuR within the four corresponding fragments demonstrate that HuR binds to frame 2 within (AUUU)₃A. This frame is consistent with the HuD motif, but 5'terminally elongated by one uracil residue, suggesting the preliminary binding motif NN(U/C)UNN(U/C)U(U/C). Fragments 5, 6, 7a-7d and 8a-8c serve to tests tolerance for non-Uracil (exemplified by A=adenine) and C, respectively, at the depicted (bold and underlined) positions. In consequence we found that HuR sequence binding motif is NNUUNNUUU. This interaction appears to follow an all-or-nothing mechanism: While sequences with single mismatches are not recognized, sequences fulfilling this motif are bound with high affinity and an invariable Kd, $Kd_{fund}$, of 0.99 nM.

TABLE 2

| RNA fragment No | nucleotides | Kd (in nM) |
|---|---|---|
| 1 | U U U U U U U U | not bound |
| 2 | U U U U U U U U U | 0.97 +/- 0.19 |
| 3 | (AUUU)₂A | not bound |
| 4a | (AUUU)₃A | 1.40 +/- 0.39 |
| 4a | A U U U A U U U A U U U A | not bound |
| 4b | A U U U A U U U A U U U A | 0.77 +/- 0.25 |
| 4c | A U U U A U U U A U U U A | not bound |
| 4d | A U U U A U U U A U U U A | not bound |
| prel. consensus | N N U/C U N N U/C U U/C | |
| 7a | U A U U U U U U | not bound |
| 7b | U A U A U U U U U | not bound |
| 7c | U A U U U U A U U | not bound |
| 7d | U A U U U U U A U | not bound |
| 8a | U A C U U U U U U | not bound |
| 8b | U A U U U U U U C | not bound |
| 8c | U A U U U U C U U | not bound |
| 5 | U A U U A U U U U | 1.14 +/- 0.24 |
| 6 | A A U U U A U U U | 1.01 +/- 0.27 |
| MOTIF | N N U U N N U U U | |

The invention claimed is:

1. A method for identifying an inhibitor of complex-formation of an AU-rich element (ARE)-containing mRNA and an Hu-Antigen R (HuR) protein comprising:
   a providing a soluble form of a HuR protein selected from the group of proteins consisting of the amino acid sequences set forth in SEQ ID NO:3 or SEQ ID NO:4,
   (b) providing an ARE-containing mRNA,
   (c) providing a candidate inhibitor, wherein at least one of (a), (b) and (c) is labeled,
   (d) mixing the HuR protein of step (a) and the ARE-containing mRNA of step (b)
      (i) in the presence of the candidate inhibitor of step (c) and
      (ii) in the absence of the candidate inhibitor of step (c) for a sufficient period of time so that the HuR protein of step (a) and the ARE-containing mRNA of step (b) can form a complex,
   (e) detecting the amount of complexes formed in step (d) or detecting non-complexed mRNA/protein species, (f) comparing the amount of complexes formed in step (d)(ii) with the non-complexed mRNA/protein species formed in step (d)(i), and (g) identifying a candidate inhibitor that inhibits complex formation between the ARE-containing mRNA and the HuR protein.

2. The method of claim 1 characterized in that the HuR protein is provided as a homogenous solution.

3. The method of claim 1 characterized in that HuR is a soluble form of a recombinant full-length HuR protein.

4. The method of claim 1 characterized in that the mRNA fragment is fluorescently labeled.

5. The method of claim 1 characterized in that the candidate inhibitor is identified by use of a fluorescence spectroscopic method selected from the group consisting of Single Molecule Spectroscopy, Fluorescence Correlation Spectroscopy, Fluorescence Intensity Distribution Analysis, Steady-State Fluorescence Intensity, Fluorescence Anisotropy and Energy Transfer.

* * * * *

SEQUENCE LISTING

<160> NUMBER OF SEQ ID NOS: 16

<210> SEQ ID NO 1
<211> LENGTH: 326
<212> TYPE: PRT
<213> ORGANISM: human full-length sHuR
<220> FEATURE:
<221> NAME/KEY: full-length sHuR human
<222> LOCATION: (1)..(326)
<223> OTHER INFORMATION:

<400> SEQUENCE: 1

Met Ser Asn Gly Tyr Glu Asp His Met Ala Glu Asp Cys Arg Gly Asp
1               5                   10                  15

Ile Gly Arg Thr Asn Leu Ile Val Asn Tyr Leu Pro Gln Asn Met Thr
            20                  25                  30

Gln Asp Glu Leu Arg Ser Leu Phe Ser Ser Ile Gly Glu Val Glu Ser
        35                  40                  45

Ala Lys Leu Ile Arg Asp Lys Val Ala Gly His Ser Leu Gly Tyr Gly
    50                  55                  60

Phe Val Asn Tyr Val Thr Ala Lys Asp Ala Glu Arg Ala Ile Asn Thr
65                  70                  75                  80

```
Leu Asn Gly Leu Arg Leu Gln Ser Lys Thr Ile Lys Val Ser Tyr Ala
                85                  90                  95
Arg Pro Ser Ser Glu Val Ile Lys Asp Ala Asn Leu Tyr Ile Ser Gly
            100                 105                 110
Leu Pro Arg Thr Met Thr Gln Lys Asp Val Glu Asp Met Phe Ser Arg
        115                 120                 125
Phe Gly Arg Ile Ile Asn Ser Arg Val Leu Val Asp Gln Thr Thr Gly
    130                 135                 140
Leu Ser Arg Gly Val Ala Phe Ile Arg Phe Asp Lys Arg Ser Glu Ala
145                 150                 155                 160
Glu Glu Ala Ile Thr Ser Phe Asn Gly His Lys Pro Pro Gly Ser Ser
                165                 170                 175
Glu Pro Ile Ala Val Lys Phe Ala Ala Asn Pro Asn Gln Asn Lys Asn
            180                 185                 190
Val Ala Leu Leu Ser Gln Leu Tyr His Ser Pro Ala Arg Arg Phe Gly
        195                 200                 205
Gly Pro Val His His Gln Ala Gln Arg Phe Arg Phe Ser Pro Met Gly
    210                 215                 220
Val Asp His Met Ser Gly Leu Ser Gly Val Asn Val Pro Gly Asn Ala
225                 230                 235                 240
Ser Ser Gly Trp Cys Ile Phe Ile Tyr Asn Leu Gly Gln Asp Ala Asp
                245                 250                 255
Glu Gly Ile Leu Trp Gln Met Phe Gly Pro Phe Gly Ala Val Thr Asn
            260                 265                 270
Val Lys Val Ile Arg Asp Phe Asn Thr Asn Lys Cys Lys Gly Phe Gly
        275                 280                 285
Phe Val Thr Met Thr Asn Tyr Glu Glu Ala Ala Met Ala Ile Ala Ser
    290                 295                 300
Leu Asn Gly Tyr Arg Leu Gly Asp Lys Ile Leu Gln Val Ser Phe Lys
305                 310                 315                 320
Thr Asn Lys Ser His Glu
                325

<210> SEQ ID NO 2
<211> LENGTH: 325
<212> TYPE: PRT
<213> ORGANISM: Homo sapiens
<220> FEATURE:
<221> NAME/KEY: sHuR
<222> LOCATION: (2)..(325)
<223> OTHER INFORMATION:

<400> SEQUENCE: 2

Ser Asn Gly Tyr Glu Asp His Met Ala Glu Asp Cys Arg Gly Asp Ile
1               5                   10                  15
Gly Arg Thr Asn Leu Ile Val Asn Tyr Leu Pro Gln Asn Met Thr Gln
            20                  25                  30
Asp Glu Leu Arg Ser Leu Phe Ser Ser Ile Gly Glu Val Glu Ser Ala
        35                  40                  45
Lys Leu Ile Arg Asp Lys Val Ala Gly His Ser Leu Gly Tyr Gly Phe
    50                  55                  60
Val Asn Tyr Val Thr Ala Lys Asp Ala Glu Arg Ala Ile Asn Thr Leu
65                  70                  75                  80
Asn Gly Leu Arg Leu Gln Ser Lys Thr Ile Lys Val Ser Tyr Ala Arg
                85                  90                  95
```

```
Pro Ser Ser Glu Val Ile Lys Asp Ala Asn Leu Tyr Ile Ser Gly Leu
            100                 105                 110

Pro Arg Thr Met Thr Gln Lys Asp Val Glu Asp Met Phe Ser Arg Phe
            115                 120                 125

Gly Arg Ile Ile Asn Ser Arg Val Leu Val Asp Gln Thr Thr Gly Leu
            130                 135                 140

Ser Arg Gly Val Ala Phe Ile Arg Phe Asp Lys Arg Ser Glu Ala Glu
145                 150                 155                 160

Glu Ala Ile Thr Ser Phe Asn Gly His Lys Pro Pro Gly Ser Ser Glu
                165                 170                 175

Pro Ile Ala Val Lys Phe Ala Ala Asn Pro Asn Gln Asn Lys Asn Val
            180                 185                 190

Ala Leu Leu Ser Gln Leu Tyr His Ser Pro Ala Arg Arg Phe Gly Gly
            195                 200                 205

Pro Val His His Gln Ala Gln Arg Phe Arg Phe Ser Pro Met Gly Val
            210                 215                 220

Asp His Met Ser Gly Leu Ser Gly Val Asn Val Pro Gly Asn Ala Ser
225                 230                 235                 240

Ser Gly Trp Cys Ile Phe Ile Tyr Asn Leu Gly Gln Asp Ala Asp Glu
                245                 250                 255

Gly Ile Leu Trp Gln Met Phe Gly Pro Phe Gly Ala Val Thr Asn Val
            260                 265                 270

Lys Val Ile Arg Asp Phe Asn Thr Asn Lys Cys Lys Gly Phe Gly Phe
            275                 280                 285

Val Thr Met Thr Asn Tyr Glu Glu Ala Ala Met Ala Ile Ala Ser Leu
            290                 295                 300

Asn Gly Tyr Arg Leu Gly Asp Lys Ile Leu Gln Val Ser Phe Lys Thr
305                 310                 315                 320

Asn Lys Ser His Glu
                325

<210> SEQ ID NO 3
<211> LENGTH: 189
<212> TYPE: PRT
<213> ORGANISM: Homo sapiens
<220> FEATURE:
<221> NAME/KEY: HuR12
<222> LOCATION: (1)..(189)
<223> OTHER INFORMATION:

<400> SEQUENCE: 3

Met Ser Asn Gly Tyr Glu Asp His Met Ala Glu Asp Cys Arg Gly Asp
1               5                   10                  15

Ile Gly Arg Thr Asn Leu Ile Val Asn Tyr Leu Pro Gln Asn Met Thr
            20                  25                  30

Gln Asp Glu Leu Arg Ser Leu Phe Ser Ser Ile Gly Glu Val Glu Ser
            35                  40                  45

Ala Lys Leu Ile Arg Asp Lys Val Ala Gly His Ser Leu Gly Tyr Gly
        50                  55                  60

Phe Val Asn Tyr Val Thr Ala Lys Asp Ala Glu Arg Ala Ile Asn Thr
65                  70                  75                  80

Leu Asn Gly Leu Arg Leu Gln Ser Lys Thr Ile Lys Val Ser Tyr Ala
                85                  90                  95

Arg Pro Ser Ser Glu Val Ile Lys Asp Ala Asn Leu Tyr Ile Ser Gly
            100                 105                 110
```

```
Leu Pro Arg Thr Met Thr Gln Lys Asp Val Glu Asp Met Phe Ser Arg
        115                 120                 125

Phe Gly Arg Ile Ile Asn Ser Arg Val Leu Val Asp Gln Thr Thr Gly
        130                 135                 140

Leu Ser Arg Gly Val Ala Phe Ile Arg Phe Asp Lys Arg Ser Glu Ala
145                 150                 155                 160

Glu Glu Ala Ile Thr Ser Phe Asn Gly His Lys Pro Pro Gly Ser Ser
                165                 170                 175

Glu Pro Ile Ala Val Lys Phe Ala Ala Asn Pro Asn Gln
                180                 185
```

```
<210> SEQ ID NO 4
<211> LENGTH: 188
<212> TYPE: PRT
<213> ORGANISM: Homo sapiens
<220> FEATURE:
<221> NAME/KEY: HuR12
<222> LOCATION: (2)..(188)
<223> OTHER INFORMATION:

<400> SEQUENCE: 4
```

```
Ser Asn Gly Tyr Glu Asp His Met Ala Glu Asp Cys Arg Gly Asp Ile
1               5                   10                  15

Gly Arg Thr Asn Leu Ile Val Asn Tyr Leu Pro Gln Asn Met Thr Gln
            20                  25                  30

Asp Glu Leu Arg Ser Leu Phe Ser Ser Ile Gly Glu Val Glu Ser Ala
        35                  40                  45

Lys Leu Ile Arg Asp Lys Val Ala Gly His Ser Leu Gly Tyr Gly Phe
50                  55                  60

Val Asn Tyr Val Thr Ala Lys Asp Ala Glu Arg Ala Ile Asn Thr Leu
65                  70                  75                  80

Asn Gly Leu Arg Leu Gln Ser Lys Thr Ile Lys Val Ser Tyr Ala Arg
                85                  90                  95

Pro Ser Ser Glu Val Ile Lys Asp Ala Asn Leu Tyr Ile Ser Gly Leu
            100                 105                 110

Pro Arg Thr Met Thr Gln Lys Asp Val Glu Asp Met Phe Ser Arg Phe
        115                 120                 125

Gly Arg Ile Ile Asn Ser Arg Val Leu Val Asp Gln Thr Thr Gly Leu
    130                 135                 140

Ser Arg Gly Val Ala Phe Ile Arg Phe Asp Lys Arg Ser Glu Ala Glu
145                 150                 155                 160

Glu Ala Ile Thr Ser Phe Asn Gly His Lys Pro Pro Gly Ser Ser Glu
                165                 170                 175

Pro Ile Ala Val Lys Phe Ala Ala Asn Pro Asn Gln
            180                 185
```

```
<210> SEQ ID NO 5
<211> LENGTH: 34
<212> TYPE: RNA
<213> ORGANISM: Homo sapiens
<220> FEATURE:
<221> NAME/KEY: ARE sequence of human TNF-alpha
<222> LOCATION: (1)..(34)
<223> OTHER INFORMATION:

<400> SEQUENCE: 5
auuauuuauu auuuauuuau uauuuauuua uuua                            34
```

```
<210> SEQ ID NO 6
<211> LENGTH: 33
<212> TYPE: RNA
<213> ORGANISM: Homo sapiens
<220> FEATURE:
<221> NAME/KEY: ARE sequence of human IL-2
<222> LOCATION: (1)..(33)
<223> OTHER INFORMATION:

<400> SEQUENCE: 6
uauuuauuua aauauuuaaa uuuuauauuu auu                        33

<210> SEQ ID NO 7
<211> LENGTH: 33
<212> TYPE: RNA
<213> ORGANISM: Homo sapiens
<220> FEATURE:
<221> NAME/KEY: ARE sequence of IL-1 beta
<222> LOCATION: (1)..(33)
<223> OTHER INFORMATION:

<400> SEQUENCE: 7
uauuuauuua uuuauuuguu uguuuguuuu auu                        33

<210> SEQ ID NO 8
<211> LENGTH: 56
<212> TYPE: RNA
<213> ORGANISM: Homo sapiens
<220> FEATURE:
<221> NAME/KEY: ARE sequence of human IL-4
<222> LOCATION: (1)..(56)
<223> OTHER INFORMATION:

<400> SEQUENCE: 8
auuuuaauuu augaguuuuu gauagcuuua uuuuuuaagu auuuauauau uuauaa    56

<210> SEQ ID NO 9
<211> LENGTH: 26
<212> TYPE: RNA
<213> ORGANISM: Homo sapiens
<220> FEATURE:
<221> NAME/KEY: ARE sequence of human IL-8
<222> LOCATION: (1)..(26)
<223> OTHER INFORMATION:

<400> SEQUENCE: 9
uauuuauuau uuauguauuu auuuaa                                26

<210> SEQ ID NO 10
<211> LENGTH: 35
<212> TYPE: RNA
<213> ORGANISM: Homo sapiens
<220> FEATURE:
<221> NAME/KEY: ARE sequence of human Cox-2
<222> LOCATION: (1)..(35)
<223> OTHER INFORMATION:

<400> SEQUENCE: 10
uauuaauuua auuauuuaau aauauuuaua uuaaa                      35

<210> SEQ ID NO 11
<211> LENGTH: 17
<212> TYPE: RNA
<213> ORGANISM: artificial
<220> FEATURE:
<223> OTHER INFORMATION: completely artificial
```

```
<400> SEQUENCE: 11
auuuauuuau uuauuua                                                    17

<210> SEQ ID NO 12
<211> LENGTH: 21
<212> TYPE: RNA
<213> ORGANISM: artificial
<220> FEATURE:
<223> OTHER INFORMATION: completely artificial

<400> SEQUENCE: 12
auuuauuuau uuauuuauuu a                                               21

<210> SEQ ID NO 13
<211> LENGTH: 17
<212> TYPE: RNA
<213> ORGANISM: artificial
<220> FEATURE:
<223> OTHER INFORMATION: completely arificial

<400> SEQUENCE: 13
cuuucuuucu uucuuuc                                                    17

<210> SEQ ID NO 14
<211> LENGTH: 16
<212> TYPE: RNA
<213> ORGANISM: artificial
<220> FEATURE:
<223> OTHER INFORMATION: completely artificial

<400> SEQUENCE: 14
auuauuauua uuauua                                                     16

<210> SEQ ID NO 15
<211> LENGTH: 9
<212> TYPE: RNA
<213> ORGANISM: artificial
<220> FEATURE:
<223> OTHER INFORMATION: completely artificial

<400> SEQUENCE: 15 uuauuuauu                                                              9

<210> SEQ ID NO 16
<211> LENGTH: 7
<212> TYPE: RNA
<213> ORGANISM: artificial
<220> FEATURE:
<223> OTHER INFORMATION: completely artificial

<400> SEQUENCE: 16 uauuuau                                                                7
```